United States Patent [19]

Collins

[11] Patent Number: 5,098,404
[45] Date of Patent: Mar. 24, 1992

[54] HYPODERMIC SYRINGE RECEPTACLE

[76] Inventor: Evan Collins, 1950 Lesue La., Merrick, N.Y. 11566

[21] Appl. No.: 512,886

[22] Filed: Apr. 23, 1990

[51] Int. Cl.⁵ .............................................. A61M 5/32
[52] U.S. Cl. .................................. 604/199; 604/192; 604/263; 206/365; 128/919
[58] Field of Search ............... 604/110, 192, 199, 263; 206/365, 366; 128/919

[56] References Cited

U.S. PATENT DOCUMENTS

| | | | |
|---|---|---|---|
| 764,564 | 7/1904 | Dryer | 604/192 |
| 1,865,737 | 7/1932 | Baron | 215/235 |
| 2,117,469 | 5/1938 | Woodyatt | 604/199 X |
| 2,400,722 | 5/1946 | Swan | 604/192 X |
| 2,894,654 | 7/1959 | Lohrer | 215/285 |
| 3,270,743 | 9/1966 | Gingras | 604/199 X |
| 4,623,336 | 11/1986 | Pedicano et al. | 604/192 |
| 4,781,697 | 11/1988 | Slaughter | 604/192 |
| 4,840,618 | 6/1989 | Marvel | 604/187 |
| 4,883,470 | 11/1989 | Haindl | 604/192 |
| 4,921,491 | 5/1990 | Champ | 604/199 |
| 4,950,242 | 8/1990 | Alvrez | 604/110 |
| 4,950,260 | 8/1990 | Bonaldo | 604/283 |
| 4,956,907 | 9/1990 | Bruno | 29/426.5 |
| 4,986,817 | 1/1991 | Code | 604/192 |
| 5,000,742 | 3/1991 | Morrison | 604/192 |

FOREIGN PATENT DOCUMENTS

| | | | |
|---|---|---|---|
| 2620340 | 3/1989 | France | 604/192 |
| 166365 | 3/1934 | Switzerland | 604/199 |

Primary Examiner—C. Fred Rosenbaum
Assistant Examiner—Mark O. Polutta
Attorney, Agent, or Firm—Cobrin, Feingertz & Gittes

[57] ABSTRACT

Apparatus for storing prior to and after use, a hypodermic syringe which includes a hypodermic needle such that the chance of the spread of infectious disease is minimized.

1 Claim, 1 Drawing Sheet

HYPODERMIC SYRINGE RECEPTACLE

BACKGROUND OF THE INVENTION

This invention relates generally to an apparatus for safely disinfecting and storing a used hypodermic syringe.

With the great concern nowadays about the transmission of various diseases such as AIDS, great care must be taken in the handling and disposal of hypodermic syringes. The concern about the spread of AIDS has manifested itself by the fact that during many routine and more serious medical procedures the attending medical staff wears rubber gloves, face masks and takes other steps to make sure that their chance of being infected with AIDS or some other infectious disease is minimized.

Of particular concern is the handling and disposal of used hypodermic syringes. Specifically, a great concern among medical personnel is the disposal of hypodermic syringes that have been used to inject a medicament into a patient. This concern reflects the obvious fact that if the patient has an easily transmitted disease, then the medical person may inflict the disease upon himself/herself if they are pricked with the needle.

Because of this concern, great care has been taken in the disposal of used hypodermic syringes. Special containers are provided so that a used hypodermic syringe can be separated and isolated and then disposed of in a safe and efficient manner. While this technique has generally been safe in preventing a medical person from accidentally being jabbed with a used hypodermic syringe, nevertheless the need for special containers for storing used hypodermic syringes and a need to specially dispose of these containers with other potentially dangerous contents has resulted in substantial expense.

It is also desirable that prior to injecting a patient with a medicament via a hypodermic syringe that the same be carried and transported in a safe manner which minimizes the chance of a person being accidentally jabbed with the needle.

U.S. Letters Pat. No. 1,115,561 to a Frederick Northey which issued on Nov. 3, 1914 discloses an antiseptic fluid which receives the tip of a syringe prior to injection of the medicament into a patient. While the structure of Northey provides a safe manner in which to maintain the medicament in an antiseptic container, it does not treat the concern of how to safely store the syringe after the medicament has been injected into a person.

U.S. Letters Pat. No. 2,117,469 issued on May 17, 1938 to a Rollin T. Woodyatt discloses a container for a hypodermic syringe with the tip of the hypodermic needle being stored in alcohol or some other sterilant. However, this patent does not disclose a technique to safely store a used hypodermic syringe to preclude accidental jabbing of a person and the potential spread of a dangerous disease.

U.S. Letters Pat. No. 2,888,924 to Dunmire which issued on June 2, 1959 discloses a container for a hypodermic syringe which contains a well filled with an antiseptic fluid. While this protects the sterility of the hypodermic syringe prior to injection, it does not make any provision for isolating a used hypodermic syringe to prevent accidentally jabbing a person with the attendant danger.

U.S. Letters Pat. No. 2,940,445 to John Q. Adams et al., which issued on June 14, 1960, discloses a sheath and method for manufacturing the same in conjunction with protecting the needle of a hypodermic syringe. However, this patent does not disclose a disinfectant nor make provisions for disinfecting a used needle to protect against accidental transmission of an infectious disease.

U.S. Letters Pat. No. 3,270,743 to a Pierre Gingras, which issued on September 6, 1966, discloses a hypodermic injection syringe and more particularly a protective assembly therefor which stores the needle and a cotton wad that has an antiseptic. There is no teaching, however, of safely storing a used hypodermic needle and disinfecting the same to protect against accidental transmission of a disease.

U.S. Letters Pat. No. 3,354,881 to Herman Bloch issued on Nov. 28, 1967 and discloses a hypodermic needle protector comprising a flexible walled tube which contains a disinfectant. However, no means are disclosed for protecting and disinfecting the needle after use nor for guiding the used needle into a disinfectant so as to minimize the chances of a person being accidentally pricked.

U.S. Letters Pat. No. 4,416,663 to Robert M. Hall issued on Nov. 22, 1983 and discloses a self-sterilizing hypodermic syringe. The needle is designed for repeated use and after each use the needle tip passes through a self-sealing capsule containing a sterilizing fluid.

SUMMARY OF THE INVENTION

It is an object of the present invention to provide an improved method and apparatus for safely disinfecting and storing a used hypodermic syringe.

A more specific object of the present invention is to provide a method and apparatus for disinfecting in a safe manner a used hypodermic syringe so that the same can be disposed of without the need for elaborate safeguards which heretofore have characterized the prior art.

Yet another object of the present invention is to provide an improved method and apparatus for disinfecting a used hypodermic syringe wherein the chances of a person being accidentally pricked by the used hypodermic needle are minimized and the used hypodermic needle is conveniently disinfected and stored in a safe and secure manner after use.

Still another object of the present invention is to provide apparatus for safely storing a hypodermic syringe prior to use and for disinfecting the hypodermic needle after use so that the hypodermic syringe can be disposed of without the need for elaborate safeguards that have heretofore characterized the prior art.

Another object of the present invention is to provide a container for safely securing a hypodermic syringe prior to use, and for enabling the needle of the hypodermic syringe to be disinfected after use while preventing the accidental pricking of a person's skin.

Other objects of the present invention will be appreciated by those having skill in the art.

Briefly, the foregoing, as well as other objects, are achieved by a hypodermic syringe receptacle. The hypodermic syringe receptacle includes at one end a guide means for receiving the needle of a hypodermic syringe after it has been used. At the other end of the hypodermic syringe receptacle is a needle syringe can be inserted into a storage contianer prior to use. Separating the storage container from the guide means is a disinfectant pad.

The disinfectant pad contains a disinfectant such that when the hypodermic needle is passed therethrough the same is disinfected.

Prior to use, the hypodermic needle is inserted into the storage container through the needle permeable material. When it is desired to use the hypodermic needle, the same is removed from the storage container and the needle withdrawn from the needle permeable material.

After the hypodermic syringe has been used, the needle is guided by the guide means through the disinfectant pad so that, to the extent there are any germs on the needle, they are rendered innocuous. The needle then is extended into the storage container where it remains protected from accidentally pricking a person's skin. Because the hypodermic syringe and specifically the needle has been disinfected, it can be discarded without concern that special precautions must be taken to prevent the spread of a potentially infectious disease.

DETAILED DESCRIPTION OF THE PREFERRED EMBODIMENT

Figure 1:
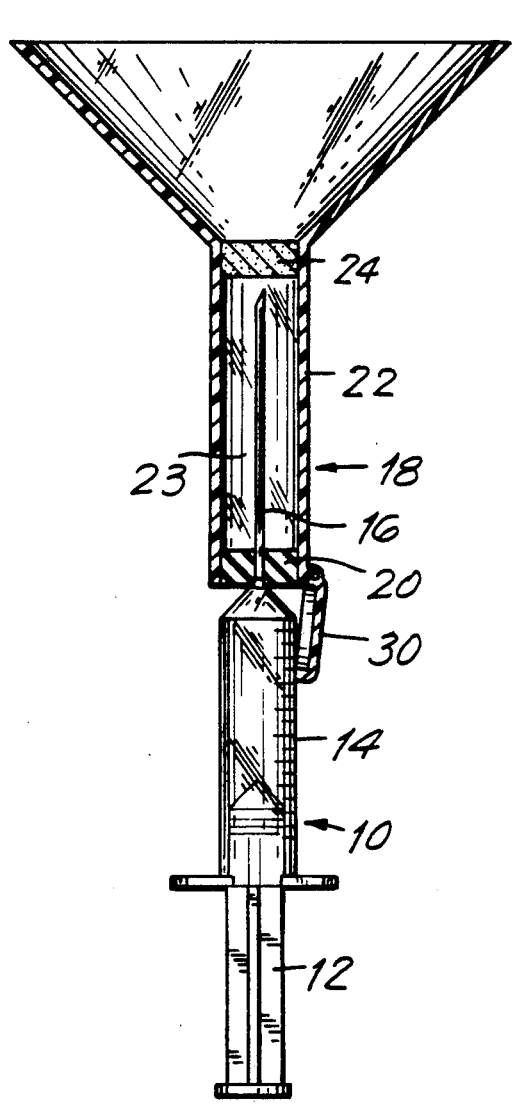
FIG. 1 is a sectional view of a hypodermic syringe receptacle in accordance with the present invention showing the hypodermic syringe prior to use.

In FIG. 1 of the drawings, a hypodermic syringe receptacle according to the present invention is shown and denominated by the reference numeral 18. The hypodermic syringe receptacle 18 is designed to cooperate with a standard hypodermic syringe 10. Hypodermic syringe 10 includes a plunger 12, a barrel 14 and a hollow needle 16. The hypodermic syringe shown in the drawings is for illustrative purposes only and the hypodermic syringe receptacle of the present invention could be used with any type of hypodermic syringe currently on the market.

Hypodermic syringe receptacle 18 includes a cylinder 22 which defines in its interior a storage container 23. Located at a first end 21 of cylinder 22 is a needle permeable member 20 through which a hypodermic needle can be extended. Located at the second or distal end of cylinder 22 is a pad 24 which contains a disinfectant. Alternatively, a sealed disinfectant chamber can be used which is needle permeable. Pad 24 can be constructed of any needle permeable material and the disinfectant therein will be obvious to those having ordinary skill in the art and is intended to immediately disinfect and kill any germs, bacteria and/or other diseases on needle 16 upon the same being passed into container 24.

Located adjacent container 24 is a conical guide means 28.

Figure 2:
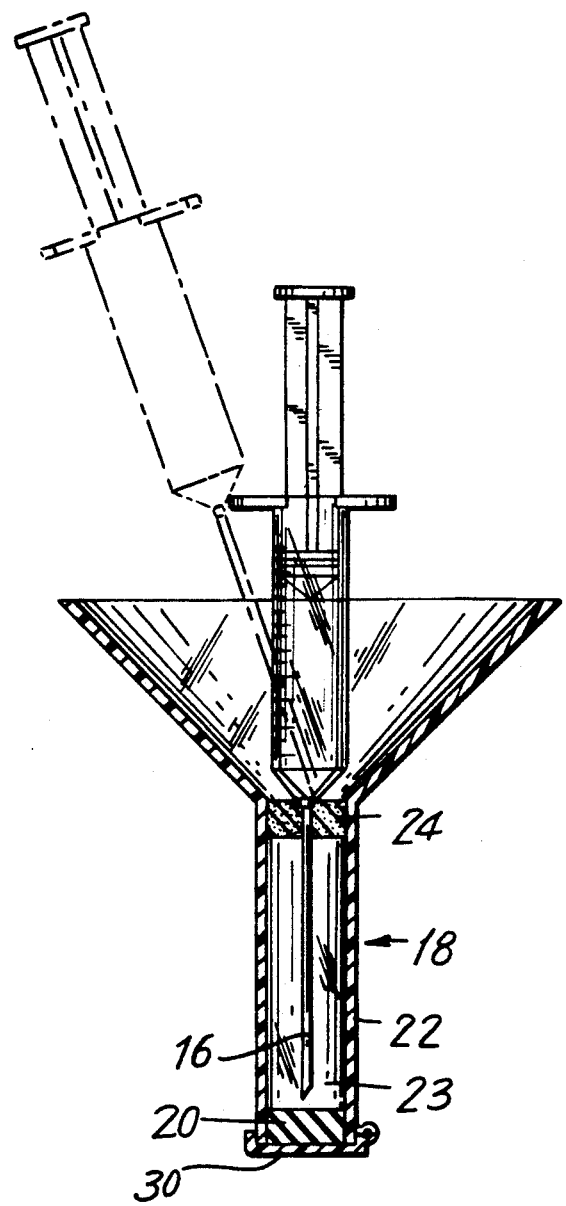
FIG. 2 is a sectional view showing the hypodermic syringe receptacle with a hypodermic syringe located therein after use and after disinfecting.

Attached to the bottom-most portion of cylinder 22 with the hypodermic syringe receptacle 18 positioned as shown in FIG. 1 is a living hinge and cap 30 which hinge can pivot so as to cover the external surface of needle permeable material 20 by being press fit over the lower end of cylinder 22 as shown in FIG. 2.

In FIG. 1 of the drawings, hypodermic syringe 10 is positioned prior to being used to inject a medicament into a person. In FIG. 1, living hinge and cap 30 is in an open position and the hypodermic needle of hypodermic syringe 10 is located within cylinder 22 having pierced needle permeable member 20.

Hypodermic syringe receptacle 18, when used to secure a hypodermic syringe 10 prior to use, maintains the needle in a safe and sanitary condition unexposed to the environment. When it is desired to use hypodermic syringe 10, the same is removed away from hypodermic syringe receptacle 18 so that needle 16 is withdrawn through needle permeable material 20 thus making the needle available for use.

After the hypodermic syringe has been used, living hinge and cap 30 are moved to seal the open end of needle permeable material 20 as shown in FIG. 2. Hypodermic needle 18 is guided by guide means 28 as shown in FIG. 2 so that it will pierce pad 24 passing through disinfectant therein until barrel 14 abuts pad 24 as shown in FIG. 2. As the hypodermic needle passes through the disinfectant in pad 24, the needle is disinfected killing all viruses, germs, etc. that may be thereon.

Guide means 28 prevents accidental pricking of a person's skin as the needle is being guided through pad 24.

After the hypodermic needle of hypodermic syringe 10 has passed through the disinfectant in pad 24, the needle is no longer a carrier or transmitter of disease and the entire hypodermic syringe and hypodermic syringe receptacle as shown in FIG. 2 may be discarded in appropriate trash without special care having to be taken to protect against the accidental transmission of diseases. Thus, it can be seen that the need for special disposal containers to store used hypodermic syringe needles that may contain or transmit diseases is eliminated and a less expensive disposal means, such as a garbage container, may be used to dispose of the used hypodermic syringe since the needle has been disinfected.

Having described specific preferred embodiments of the invention with reference to the accompanying drawings, it will be appreciated that the present invention is not limited to those precise embodiments, and that various changes and modifications can be effected therein by one of ordinary skill in the art without departing from the spirit or scope of the invention as defined in the appended claims.

What is claimed is:

1. Apparatus for storing a hypodermic syringe which includes a hypodermic needle prior to and after use, comprising:
    a storage member defining a storage space, said storage member having a first end and a second end;
    a first needle-permeable member defining said first end of said storage member and containing a disinfectant fluid for disinfecting a hypodermic syringe needle after use;
    a second needle-permeable member defining said second end of said storage member;
    closure means adjacent said second end of said storage member and pivotably connected to said storage member for selectively sealing said second needlepermeable member; and
    means extending away from and flaring outwardly from said first needlepermeable member for guiding the hypodermic syringe needle of a used hypodermic syringe that has expelled its contents such that the hypodermic syringe needle is guided through said first needle-permeable member through said disinfectant and into said storage member for preventing said hypodermic needle from accidentally picking the skin of a person.

* * * * *